(12) United States Patent
Ranasinghe et al.

(10) Patent No.: US 11,564,762 B2
(45) Date of Patent: Jan. 31, 2023

(54) ALIGNED GLOVES

(71) Applicant: Ansell Limited, Richmond (AU)

(72) Inventors: Lakshmie Swarnamala Ranasinghe, Kelaniya (LK); Sakala Walli Acharige Samantha Pradeep Laksiri, Kuliyapitiya (LK); Koralalage Don Sugathananda Amarasekera, Ethuel Kotte (LK)

(73) Assignee: Ansell Limited, Victoria (AU)

( * ) Notice: Subject to any disclaimer, the term of this patent is extended or adjusted under 35 U.S.C. 154(b) by 592 days.

(21) Appl. No.: 16/605,114

(22) PCT Filed: May 22, 2018

(86) PCT No.: PCT/AU2018/000075
§ 371 (c)(1),
(2) Date: Oct. 14, 2019

(87) PCT Pub. No.: WO2018/213865
PCT Pub. Date: Nov. 29, 2018

(65) Prior Publication Data
US 2021/0137625 A1    May 13, 2021

Related U.S. Application Data

(60) Provisional application No. 62/509,302, filed on May 22, 2017.

(51) Int. Cl.
*A61B 42/40* (2016.01)
*A61B 42/50* (2016.01)
*A61B 42/10* (2016.01)
*A41D 19/00* (2006.01)

(52) U.S. Cl.
CPC ............ *A61B 42/50* (2016.02); *A41D 19/001* (2013.01); *A61B 42/10* (2016.02); *A61B 42/40* (2016.02); *A41D 19/0062* (2013.01); *A41D 2400/44* (2013.01)

(58) Field of Classification Search
CPC ........ A61B 42/40; A61B 42/10; A41D 19/001
See application file for complete search history.

(56) References Cited

U.S. PATENT DOCUMENTS

| | | | | |
|---|---|---|---|---|
| 3,181,695 A | * | 5/1965 | Taterka | A61B 42/40 229/87.16 |
| 3,384,225 A | * | 5/1968 | Nye | B65D 75/38 229/87.16 |
| 3,391,855 A | * | 7/1968 | Ansell | B65D 75/38 229/87.16 |

(Continued)

FOREIGN PATENT DOCUMENTS

| CN | 205390433 U | 7/2016 |
|---|---|---|
| WO | WO 03-020109 A2 | 3/2003 |
| WO | WO-03020109 A2 | 3/2003 |

OTHER PUBLICATIONS

Extended European Search report for Application No. 18805543.8 dated Feb. 8, 2021, 10 pgs.

(Continued)

*Primary Examiner* — Tajash D Patel
(74) *Attorney, Agent, or Firm* — Moser Taboada

(57) ABSTRACT

A glove-in-glove having aligned features is disclosed.

20 Claims, 7 Drawing Sheets

(56) References Cited

U.S. PATENT DOCUMENTS

| | | | | |
|---|---|---|---|---|
| 3,412,851 | A | * | 11/1968 | Coulombe ............. A61B 42/40 229/87.16 |
| 3,746,152 | A | * | 7/1973 | Allen .................... B65D 27/36 229/87.16 |
| 7,805,773 | B2 | | 10/2010 | Di et al. |
| 2002/0133864 | A1 | | 9/2002 | Saks et al. |
| 2006/0144878 | A1 | * | 7/2006 | Williams ............. A47G 25/904 223/111 |
| 2013/0067636 | A1 | * | 3/2013 | Howard ................ A61B 42/40 2/161.7 |
| 2013/0139294 | A1 | | 6/2013 | Zetune et al. |
| 2015/0272245 | A1 | | 10/2015 | Khor et al. |

OTHER PUBLICATIONS

International Search Report dated Sep. 28, 2018 for application PCT/AU2018/000075.

\* cited by examiner

ALIGNED GLOVES

FIELD

This disclosure is directed to personal protective equipment and, more specifically, to a glove-in-glove having aligned features.

BACKGROUND

Polymeric gloves, such as surgical and examination gloves, are made of strong but flexible elastomers, which permit a snug fit to hands. Polymeric gloves are often formed in a shape that approximates the shape of a flattened hand. However, gloves made in this shape are not ergonomic. Furthermore, surgeons wearing surgical gloves may do so for long durations during procedures, which tire the surgeon's fingers and/or hands because the elastic modulus of the elastomer, of which the glove is made, must be overcome to flex or bend the fingers. Moreover, the flexure of fingers may be impeded at the knuckles on both a palmside and a backhand side. Also, in an attempt to relieve stresses, some wearers use oversized gloves, which unfortunately cause a loss of dexterity and grip, particularly at the fingertips. Furthermore, surgeons and other medical personnel often "double-glove" to provide extra barrier protection, leading to increased fatigue for wearers because of additional forces that must be overcome to flex the hands. The material of the double-gloves can bunch in certain areas, such as at the finger tips, the crotches between adjacent fingers or the index finger and the thumb, making flexing difficult.

Therefore, a glove-in-glove that is aligned can prevent additional stresses on wearers without loss of tactility and dexterity, representing an advance in the art.

SUMMARY

Embodiments according to the disclosure include a glove-in-glove having aligned features, substantially as shown in and/or described in connection with at least one of the figures, as set forth more completely in the claims, are disclosed. Various advantages, aspects, and novel features of this disclosure will be more fully understood from the following description and drawings.

The foregoing summary is not intended, and should not be contemplated, to describe each embodiment or every implementation of the disclosure. Other and further embodiments are described below.

BRIEF DESCRIPTION OF THE DRAWINGS

So that the manner in which the above recited features of the disclosure can be understood in detail, a more particular description of embodiments, briefly summarized above, may be had by reference to some embodiments, some of which are illustrated in the appended drawings. It is to be noted, however, that the appended drawings illustrate only typical embodiments and are therefore not to be considered limiting of its scope, for the disclosure may admit to other equally effective embodiments. It is to be understood that elements and features of one embodiment may be in other embodiments without further recitation. It is further understood that, where possible, identical reference numerals have been used to indicate comparable elements that are common to the figures.

DETAILED DESCRIPTION

Figure 1:
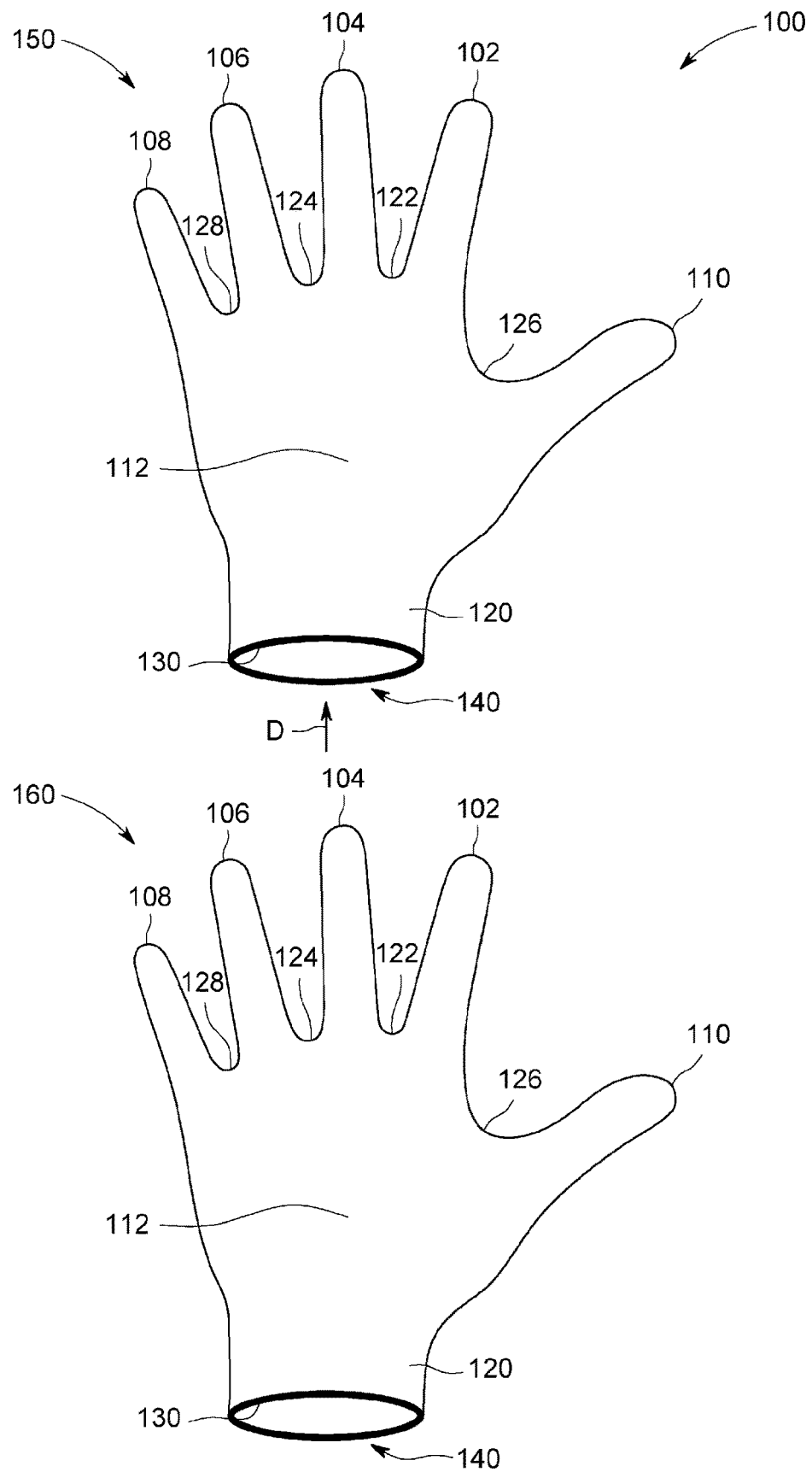
FIG. 1 depicts an exploded view of an aligned glove-in-glove, according to embodiments discussed within this disclosure.

Embodiments of the glove-in-glove embodiments discussed herein comprise dipped gloves, such as examination gloves, surgical gloves, and gloves for industrial and household use. The glove-in-glove has aligned features corresponding to regions of the human hand, such as crotches between, for example, the index finger and the middle finger, the middle finger and the ring finger, the index finger and the thumb, finger tips, and the like. In this manner, a glove that is disposed within a glove can be aligned. Crotches that are aligned reduce stresses on the human hand during flexing and prolonged periods of use while remaining tight and snug where needed, e.g., fingertips. Furthermore, embodiments of the glove-in-gloves comprise an alignment of the cuff and/or bead areas. Thicker gloves, which are also within the scope of embodiments of the aligned glove-in-gloves according to embodiments, are disclosed. Embodiments also comprise a glove-in-glove in which an inner glove is one-half to one size larger than an outer glove. Embodiments also comprise a glove-in-glove in which an inner glove is one-half to one size larger and/or has a thinner cross-sectional thickness than an outer glove. Embodiments also comprise a glove-in-glove in which an inner glove is one-half to one size larger and/or has a substantially similar cross-sectional thickness compared with an outer glove. Embodiments also comprise a glove-in-glove in which an inner glove is one-half to one size larger and/or has a thicker cross-sectional thickness than an outer glove, wherein the donning of the glove-in-glove is facilitated. An inner glove that is thinner than the outer glove can be suitable for ease of donning and doffing of the glove-in-glove. An inner glove that is thicker than the outer glove provides superior barrier protection. Having a glove disposed within a glove and packaged in this manner allows doctors and other users to don the glove more quickly, with less stress to the hands of the doctor, and with less force on the gloves, promoting fewer breaches. Furthermore, donning two gloves simultaneously saves time, and generates less packaging waste compared to the regular double gloving.

Embodiments in which the gloves are substantially the same size can use an inner glove that is thinner than the outer glove, providing comfort more like that found with the inner glove being slightly larger than the outer glove. This approach thus provides the comfort of the inner larger approach, but without the finger-tip bunching that can be an issue with the latter approach.

Before describing embodiments of the present disclosure in detail, the terminology used herein is for the purpose of describing particular embodiments only, and is not intended to be limiting. Embodiments should not necessarily be limited to specific compositions, materials, sizes, designs or equipment, as such may vary. All technical and scientific terms used herein have the usual meaning conventionally understood by persons skilled in the art to which this disclosure pertains, unless context defines otherwise. Also, as used in this specification and the appended claims, the singular forms "a," "an," and "the" include plural referents unless the context clearly dictates otherwise.

The term "align," or "aligned" in the context of this disclosure indicates at least one of that the fingertips of an inner glove and an outer glove are in contact or close to intimate contact, particularly while being worn by a user and/or that the crotches of an inner glove and an outer glove between adjacent fingers and/or index finger and a thumb are in contact or close to intimate contact, particularly while being worn by a user.

The term "flexing" or "flex" refers to finger movements, such as bending fingers, making a fist, gripping, grasping, clenching or otherwise folding the fingers.

FIG. 1 depicts an exploded view of an aligned glove-in-glove 100, according to embodiments discussed within this disclosure. The aligned glove-in-glove 100 comprises an outer glove 150 and an inner glove 160. Each of the outer glove 150 and the inner glove 160 comprises a thumb 110, a plurality of fingers, e.g., an index finger 102 a middle finger 104, a ring finger 106, and a little finger 108, a palm region 112, a backhand region (not shown), and a cuff 120. Each of the outer glove 150 and inner glove 160 the glove-in-glove 100 optionally comprises a bead 130 proximate an opening 140 for receiving a hand of a wearer. Each of the outer glove 150 and the inner glove 160 further comprises finger crotches 122, 124, and 128 and thumb-index finger crotch 126. As depicted, the outer glove 150 is smaller than the inner glove 160, for example, by half a glove size. As shown further below, embodiments also comprise wherein the inner glove 160 and the outer glove are the same size. Furthermore, embodiments also include wherein the inner glove 160 is smaller than the outer glove 150. The inner glove 160 is placed into the outer glove 150 and packaged in a paper or foil container and/or the like, as is known to those in the art. For example, by automated processes or manually, the inner glove 160 is placed into outer glove 150 by forcing the inner glove 160 into the outer glove 150 at direction D. The inner glove 160 may be on a former or mandrel or any other appropriate mold as is known to those in the art. The inner glove 160 is placed into the outer glove 150 so that the crotches 122, 124, 128, and 126 are aligned. Furthermore, in some embodiments, the beads 130 are aligned after disposition of the inner glove 160 into the outer glove 150.

Figure 2:
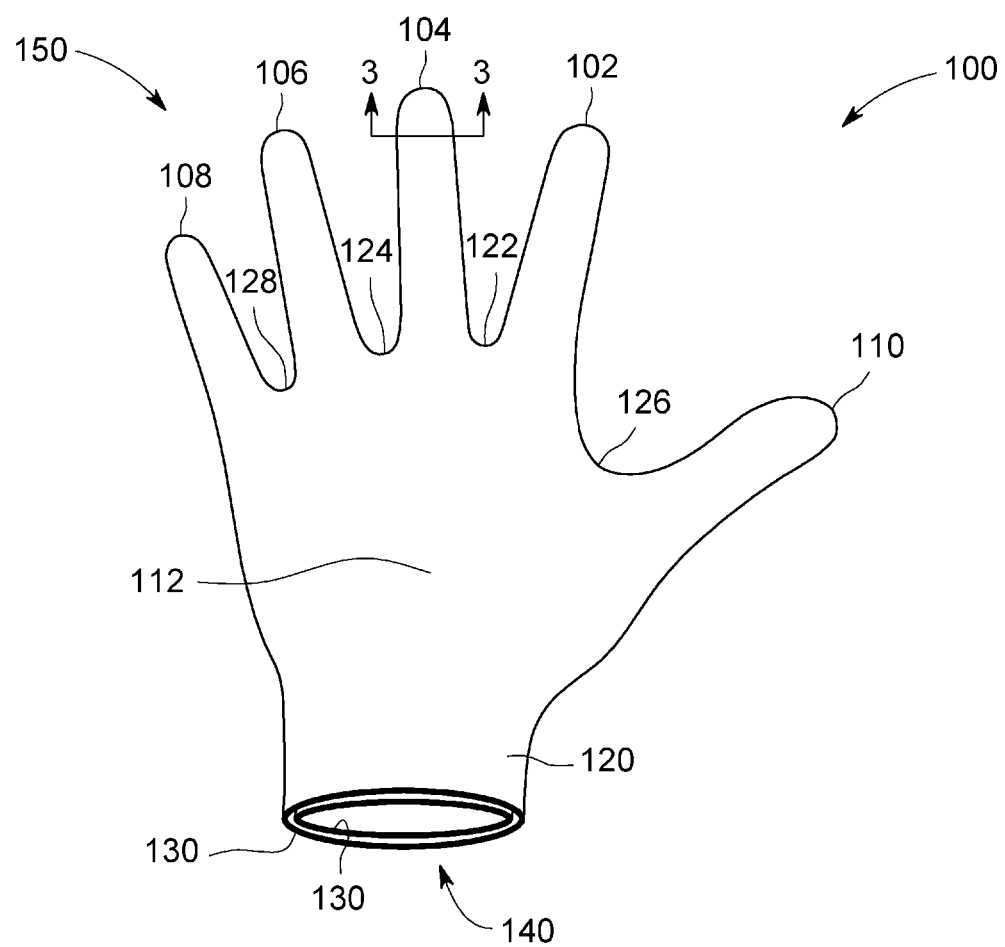
FIG. 2 depicts the aligned glove-in-glove of FIG. 1, according to embodiments discussed within this disclosure.

FIG. 2 depicts the aligned glove-in-glove 100 of FIG. 1, according to embodiments discussed within this disclosure. As shown, the bead 130 of the inner glove 160 is shown aligned with the bead 130 of the outer glove 150.

Figure 3:
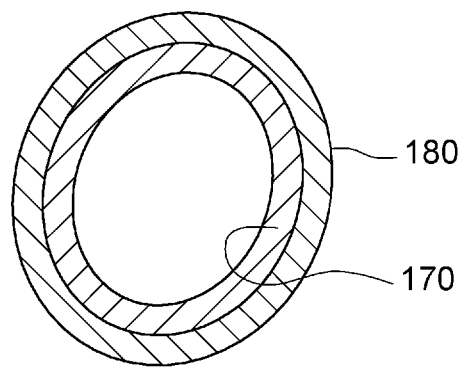
FIG. 3 depicts a cross-section view of a finger of the aligned glove-in-glove of FIG. 1, according to embodiments discussed within this disclosure.

FIG. 3 depicts a cross-section view of a finger 104 of the aligned glove-in-glove 100 of FIG. 1, according to embodiments discussed within this disclosure. The fingertip 170 is a cross sectional view of the middle finger 104 of the inner glove 160. The fingertip 180 is a cross sectional view of the middle finger 104 of the outer glove 150. As can be seen, the fingertip 180 and the fingertip 170 are aligned, i.e., in close contact.

Figure 4A:
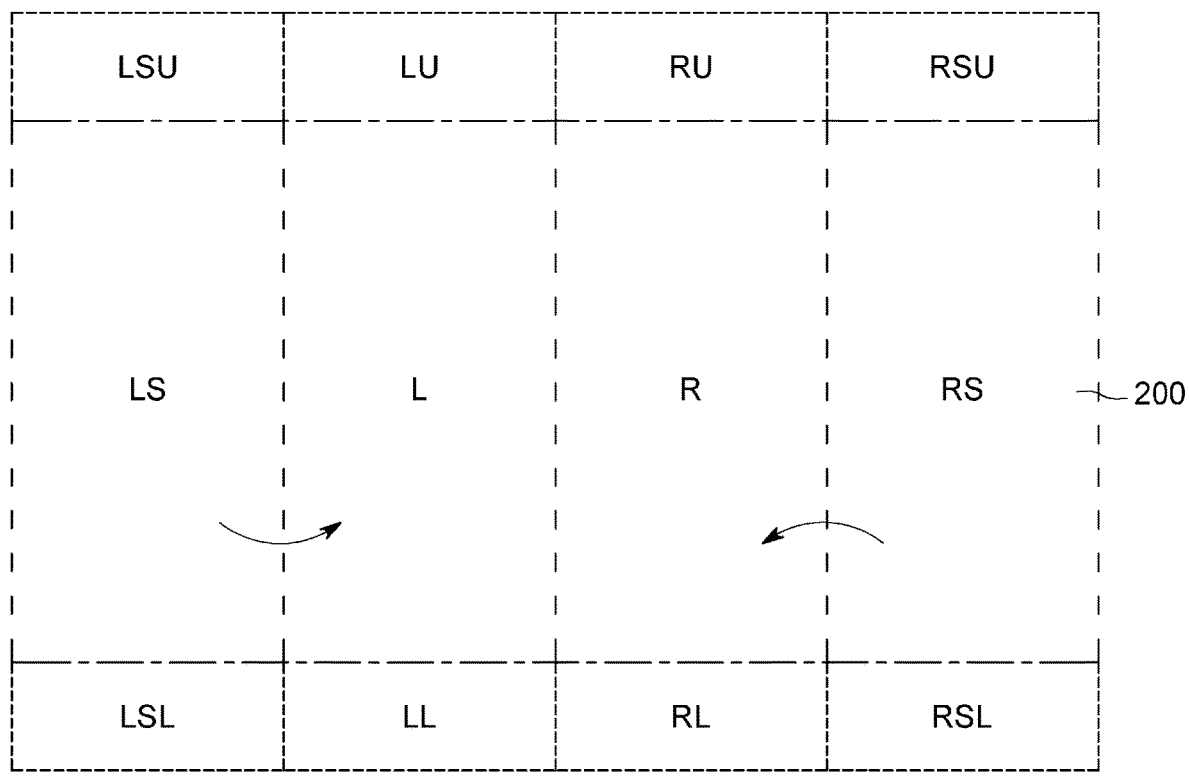
FIGS. 4A-4E illustrate how gloves can be enfolded in a material sheet.

FIG. 4A shows an illustrative material sheet 200 (e.g. paper coated with a thin plastic layer on one or both sides) unfolded, but with fold lines indicated. Panel R is where the right glove is presented on unfolding. Panel RS is that which immediately covers the glove. Panels RL, RU, RSL and RSU complete the right side. Complementary panels beginning with L are for the left glove. An illustrative first fold (arrow) for enfolding is shown.

Figure 4B:
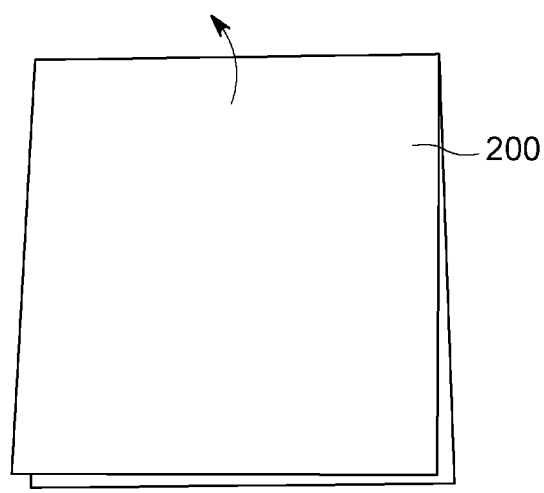
Figure 4C:
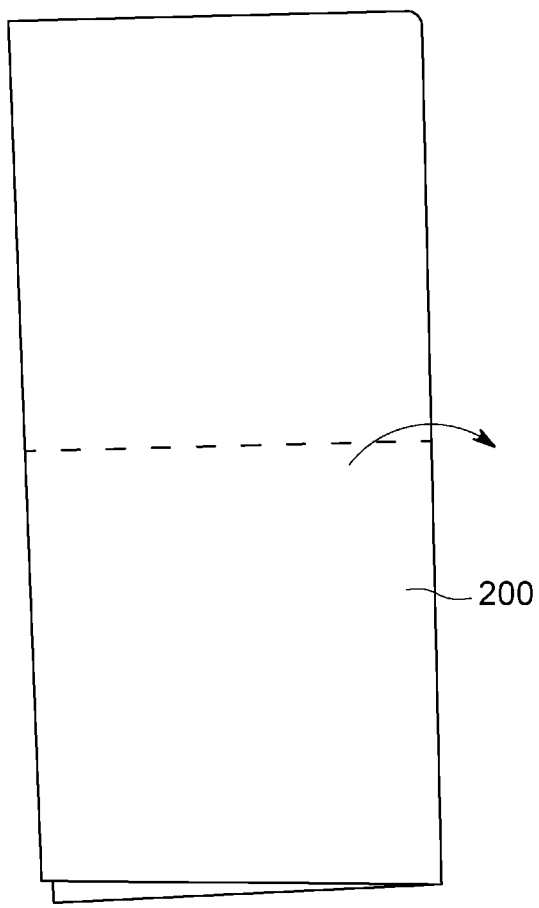
Figure 4D:
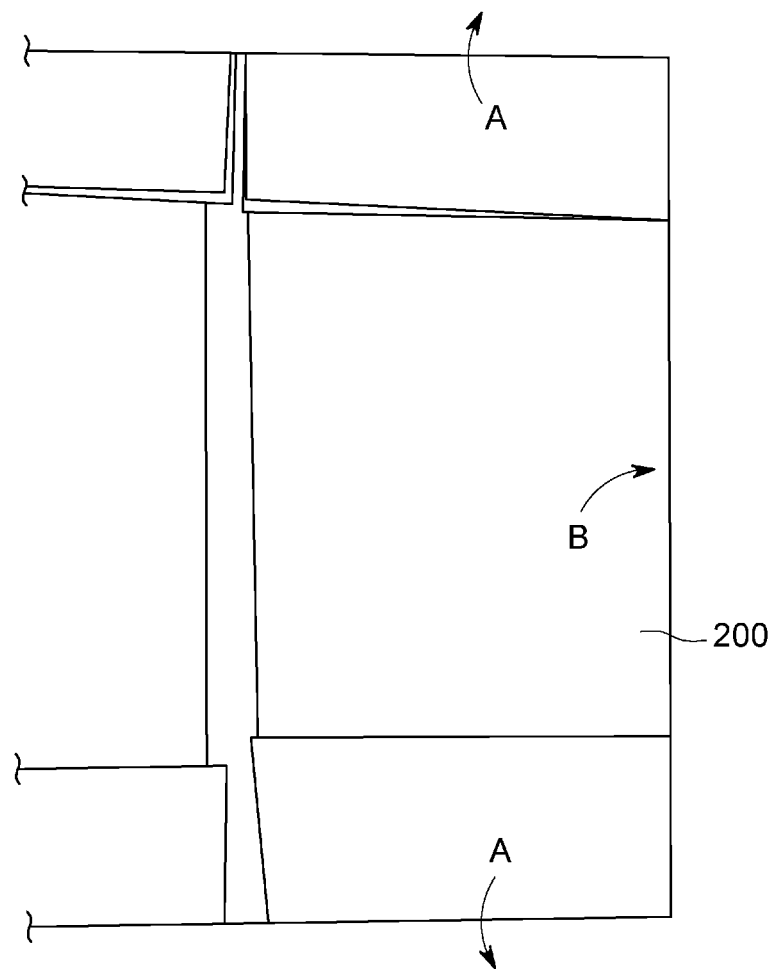
Figure 4E:
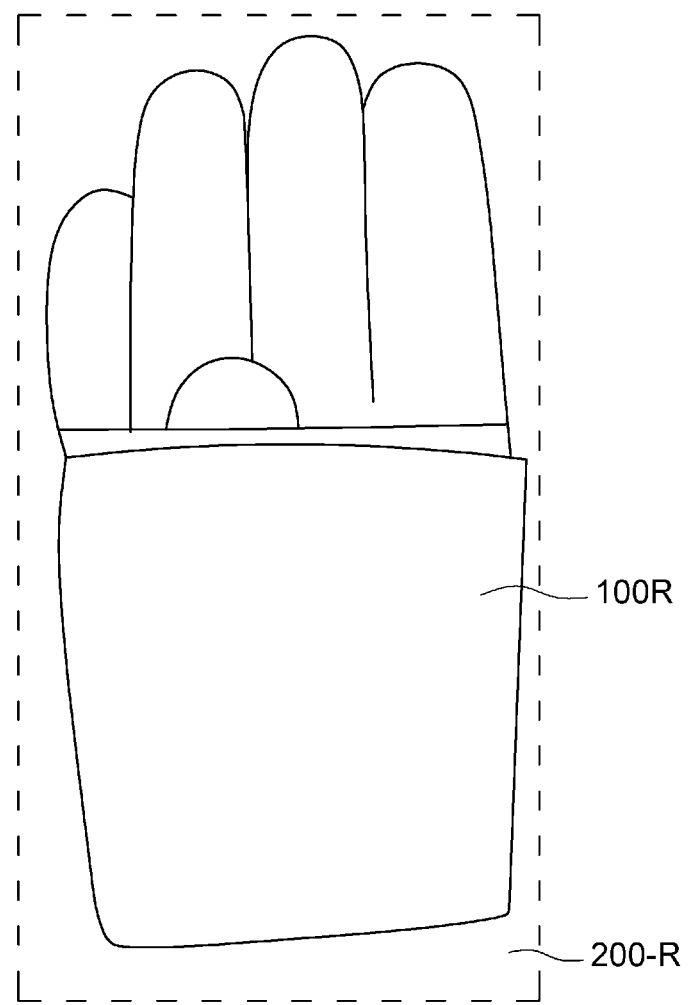

FIG. 4B shows the fully folded material sheet 200, with the first fold for unfolding shown. FIG. 4C shows the next fold for unfolding. FIG. 4D shows the next folds (A), and the subsequent fold (B) for unfolding. FIG. 4E shows glove-in-glove 100R, which is cuff folded to facilitate donning. The fully folded material sheet 200 can for example be vacuum sealed within a plastic or metalized covering. Sterilization can be prior to sealing followed by sterile practice in the sealing, or post-sealing, such as by radiation.

Table 1 shows various combinations of sizes of inner and outer gloves. Synthetic polyisoprene gloves have thicknesses for example of approximately 0.24 mm at the fingers, approximately 0.21 mm at the palm region, and approximately 0.19 mm at a cuff region. Neoprene or polychloroprene gloves have thicknesses of approximately 0.20 mm at the fingers, approximately 0.19 mm at the palm region, and approximately 0.16 mm at a cuff region. Synthetic polyisoprene "Micro" gloves can have thicknesses that is as much as approximately up to 10%, or 20%, or 30% thinner than the above mentioned gloves, for example, approximately 0.18 mm to approximately 0.21 mm (such as about 0.19 to about 0.21 mm, or about 0.18 mm) at the fingers, approximately 0.16 mm to approximately 0.19 mm (such as about 0.17 mm) at the palm region, and approximately 0.13 mm to approximately 0.18 mm (such as about 0.14 to about 0.18 mm, or about 0.13 mm) at a cuff region. Micro gloves may be particularly suited for use as an inner glove. Irrespective of size or type (natural rubber, synthetic polyisoprene, polychloroprene, and other various synthetic materials), the length of the gloves is typically approximately 295 to approximately 310 mm. Where a hybrid polymer of polyisoprene and chloroprene is used, exemplary glove thicknesses can be about 0.18 mm to about 0.23 mm at the fingers, about 0.16 mm to about 0.21 mm at the palm, and about 0.13 mm to about 0.18 mm at the cuff.

TABLE 1

Exemplary Glove combinations

| Option | Inner Glove (Under Glove) | Outer glove (Top Glove) | Thickness (mm) Finger | Thickness (mm) Palm | Thickness (mm) Cuff |
|---|---|---|---|---|---|
| 1 | Synthetic (Non latex) | Synthetic (Non latex) | 0.20 | 0.19 | 0.16 |
| 2 | Natural rubber (Latex) | Natural rubber (Latex) | 0.24 | 0.21 | 0.19 |
| 3 | Synthetic (Non latex) | Natural rubber (Latex) | | | |
| 4 | Natural rubber (Latex) | Synthetic (Non latex) | | | |

Glove size is determined by the industry-accepted extrapolation from the circumference of the hand measured just below the knuckles, in inches. If the measurement rounded to the nearest ½ inch is for example 7.5 inches, then a size 7.5 glove is configured for that hand, and so forth. For the purpose of fitting a larger glove in a smaller glove, or a smaller glove in a larger glove, smaller size differentials can be used, such as ¼ sizes.

Option 1 (½ a size larger inner, both fingers & crotches align)

TABLE 2

| Size | Outer glove (Top Glove) | Inner Glove (Under Glove) |
|---|---|---|
| 5.5 | 5.5 | 6.0 |
| 6.0 | 6.0 | 6.5 |
| 6.5 | 6.5 | 7.0 |
| 7.0 | 7.0 | 7.5 |
| 7.5 | 7.5 | 8.0 |
| 8.0 | 8.0 | 8.5 |
| 8.5 | 8.5 | 9.0 |

Option 2 (Both gloves same size, fingers, crotches & bead align)

TABLE 3

| Size | Outer glove (Top Glove) | Inner Glove (Under Glove) |
|---|---|---|
| 5.5 | 5.5 | 5.5 |
| 6.0 | 6.0 | 6.0 |
| 6.5 | 6.5 | 6.5 |
| 7.0 | 7.0 | 7.0 |
| 7.5 | 7.5 | 7.5 |
| 8.0 | 8.0 | 8.0 |
| 8.5 | 8.5 | 8.5 |
| 9.0 | 9.0 | 9.0 |

Option 3 (½ a size smaller inner, both fingers & crotches align)

TABLE 4

| Size | Outer glove (Top Glove) | Inner Glove (Under Glove) |
|---|---|---|
| 6.0 | 6.0 | 5.5 |
| 6.5 | 6.5 | 6.0 |
| 7.0 | 7.0 | 6.5 |
| 7.5 | 7.5 | 7.0 |
| 8.0 | 8.0 | 7.5 |
| 8.5 | 8.5 | 8.0 |
| 9.0 | 9.0 | 8.5 |

Tables 2, 3, and 4 show options of various sized gloves combinations of an inner glove and an outer glove. For example, in Table 2, option 1, the inner glove is ½ a size larger than the outer glove, wherein placing the inner glove on the hand and the outer glove over the inner glove allows both the fingers and the finger crotches to align. In Table 3, option 2 the inner glove and the outer glove are the same size, wherein the fingers, the finger crotches and the bead align.

In Table 4, option 3, the inner glove is ½ a size smaller than the outer glove, wherein placing the inner glove on the hand and the outer glove over the inner glove allows the finger crotches to align, and can allow the finger tips to align.

The gloves can be packaged folded in a foldable material configured to unfold and present on the foldable material a right glove on one side, and a left glove on the other side, provided the gloves and foldable material are laid out with the fingers pointed away from the prospective user.

An "ergonomic" glove is one made off an ergonomic former, as will be recognized by those of skill in the surgical glove arts. Examples can be described with respect to an uplifted hand with the fingers spread consistent with the spread of a relaxed hand, where the thumb is positioned inwards of the position it would have if positioned in the plane with the four remaining fingers, and thus positioned, consistent with the anatomical linkages of the hand, in front of rough axis defined by the palmar digital crease (the base of remaining fingers). Looking at the hand from a position orthogonal to the up/down axis of the hand and orthogonal to the above described rough axis, the thumb is positioned from approximately in line with the index finger to a location to the outside that is approximately ½ times the distance of the index finger to the middle finger. An ergonomic glove is configured to best conform to such a hand. In embodiments, the modeling hand has fingers curved inwards as would apply for a hand with the fingers in a relaxed position.

The terms "emulsion," "dispersion," and "suspension" are generally analogous and indicate a system in which small particles of a substance, such as rubber particles, are mixed with a fluid (such as water and/or alcohols and/or other organic fluids) but are at least partially undissolved and kept dispersed by agitation (mechanical suspension) and/or by the molecular forces in a surrounding medium (colloidal suspension). Emulsions contemplated herein may further comprise typical and suitable components for rubber or elastomeric formulations and compounds, such as accelerators, such as guanidines, thiazoles, thiurams, sulfenamids, thioureas, dithiocarbamates, and xanthanates, surfactants, such as sodium dodecyl sulfates and polyvinyl alcohols, activators, such as zinc oxides, cross-linking agents and curatives, such as elemental sulfur and/or polysulphidic donors, anti-oxidants, anti-ozonants, rheology-modifiers, such as various clays and aluminosilicates, pH adjusters, such as hydroxides, such as potassium hydroxide, pigments, processing agents, and/or fillers as are known to those in the art.

The term "polymer" generally includes, but is not limited to, homopolymers, copolymers, such as for example, block, graft, random and alternating copolymers, terpolymers, etc. and blends and modifications thereof. Furthermore, unless otherwise specifically limited, the term "polymer" includes all possible geometrical configurations of the molecule. These configurations include, but are not limited to isotactic, syndiotactic and random symmetries.

The term "thermoplastic" generally includes polymer materials that become reversibly pliable, moldable, and/or heatable above a specific temperature and solidify upon cooling. The term "thermoset" generally includes polymer materials that strengthen following heating and solidification, but cannot be successfully remolded or otherwise processed after an initial heat-forming. The term "thermoplastic elastomer" (TPE) connotes a class of copolymers comprising both thermoplastic and elastomeric/thermoset material properties and generally have crosslinking between adjacent polymeric molecular chains. The term "rubber" generally indicates elastomers produced from natural rubber latexes or synthetic elastomers.

Exemplary thermoplastics include, without limitation, polychloroprenes, butyl rubbers, natural rubber, synthetic polyisoprenes, poly(vinyl) chlorides, polyesters, polyamides, polyfluorocarbons, polyolefins, polybutadienes, polyurethanes, polystyrenes, poly(vinyl) alcohols, and copolymers of the foregoing, and elastomeric polymers such as elastic polyolefins, copolyether esters, polyamide polyether block copolymers, block copolymers having the general formula A-B-A' or A-B like nitrile-butadiene rubber (NBR), carboxylated nitrile-butadiene rubber, styrene-poly(ethylene-propylene)-styrene, styrene-poly(ethylene-butylene)-styrene, (polystyrene/poly(ethylene-butylene)/polystyrene, poly(styrene/ethylene-butylene/styrene), co-poly(styrene/ethylene-butylene), A-B-A-B tetrablock co-polymers and the like and blends of any of the foregoing. In certain embodiments, the gloves are of a hybrid polymer of polyisoprene and chloroprene with component polymer selected to yield greater translucency than a polyisoprene glove of equal thickness.

All numerical values recited herein are exemplary, are not to be considered limiting, and include ranges therebetween, and can be inclusive or exclusive of the endpoints. Optional included ranges can be from integer values therebetween, at the order of magnitude recited or the next smaller order of magnitude. For example, if the lower range value is 0.1, optional included endpoints can be 0.2, 0.3, 0.4 . . . 1.1, 1.2, and the like, as well as 1, 2, 3 and the like; if the higher range is 10, optional included endpoints can be 7, 6, and the like, as well as 7.9, 7.8, and the like.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

The invention can be further described with reference to the following numbered embodiments:

Embodiment 1: A sterilely packaged set of right and left glove-in-gloves, each glove-in-glove comprising: (A) an ergonomic outer glove having a thumb and a plurality of fingers, further comprising crotches between adjacent fingers and thumb; and (B) an ergonomic inner glove having a thumb and a plurality of fingers with finger tips, further comprising crotches between adjacent fingers and thumb, the inner glove being disposed inside the outer glove, the finger tips or the crotches of the inner glove and the outer glove being aligned; wherein the gloves are enfolded with a packaging material such that the material can be unfolded to present the right glove-in-glove on the right side and the left glove-in-glove on the left side, laid out on the packaging material.

Embodiment 2: The sterilely packaged set of gloves of one of the packaged glove embodiments [this phrase here and below references any such numbered embodiment that is not in conflict], comprising the inner gloves having a size about ¼ to 1 size units larger than the outer gloves, wherein the finger tips are aligned, and wherein the glove-in-glove provides greater user comfort than a glove-in-glove of equal size.

Embodiment 3: The sterilely packaged set of gloves of one of the packaged glove embodiments, comprising the inner gloves having a size the same as the outer gloves, wherein the finger tips and crotches are aligned.

Embodiment 4: The sterilely packaged set of gloves of one of the packaged glove embodiments, further comprising the inner gloves having a lesser cross-sectional thickness than the outer gloves, such that the glove-in-glove provides greater user comfort than a glove-in-glove of equal cross-sectional thickness.

Embodiment 5: The sterilely packaged set of gloves of one of the packaged glove embodiments, further comprising the inner gloves having a cross-sectional thickness at the center of the palm of less than 0.21 mm, such that the glove-in-glove provides greater user comfort than one with an inner glove of such thickness of 0.21 or above.

Embodiment 6: The sterilely packaged set of gloves of one of the packaged glove embodiments, further comprising the inner gloves having a cross-sectional thickness at the middle of the index finger of less than 0.24 mm, such that the glove-in-glove provides greater user comfort than one with an inner glove of such thickness of 0.24 or above.

Embodiment 7: The sterilely packaged set of gloves of one of the packaged glove embodiments, further comprising the inner gloves having a lesser cross-sectional thickness than the outer gloves.

Embodiment 8: The sterilely packaged set of gloves of one of the packaged glove embodiments, further comprising the inner glove having a cross-sectional thickness at the center of the palm of about 0.15 mm or about 0.16 mm to about 0.19 mm and the outer glove having a cross-sectional thickness at the center of the palm of about 0.16 mm to about 0.21 mm. This can include an embodiment where the inner is thinner than the outer glove.

Embodiment 9: The sterilely packaged set of gloves of one of the packaged glove embodiments, further comprising the inner glove having a cross-sectional thickness at the middle of the index finger of about 0.17 mm or about 0.19 mm to about 0.21 mm and the outer glove having a cross-sectional thickness at the middle of the index finger of about 0.18 mm to about 0.23 mm. This can include an embodiment where the inner is thinner than the outer glove.

Embodiment 10: The sterilely packaged set of gloves of one of the packaged glove embodiments, further comprising the outer glove having a lesser cross-sectional thickness than the inner glove.

Embodiment 11: The sterilely packaged set of gloves of one of the packaged glove embodiments, further comprising the outer glove having across-sectional thickness approximately equal to the inner glove.

Embodiment 12: The sterilely packaged set of gloves of one of the packaged glove embodiments, wherein the glove-in-gloves are packaged cuff-folded to facilitate donning.

Embodiment 13: The sterilely packaged set of gloves of one of the packaged glove embodiments, wherein the glove-in-gloves are packaged so that the length of the glove-in-gloves is presented after unfolding the packaging material.

Embodiment 14: The sterilely packaged set of gloves of one of the packaged glove embodiments, comprising the inner glove having a size that is one-quarter to one-half a size smaller than the outer glove, wherein the crotches and the finger tips are aligned.

Embodiment 15: The sterilely packaged set of gloves of one of the packaged glove embodiments, comprising at least one of a natural rubber latex said inner glove and a natural rubber latex said outer glove; a natural rubber latex said inner glove and a synthetic latex said outer glove; a synthetic latex said inner glove and a natural rubber latex said outer glove; or a synthetic latex said inner glove and a said synthetic latex outer glove.

Embodiment 16: The sterilely packaged set of gloves of one of the packaged glove embodiments, wherein the inner glove is colored to accentuate visual recognition of liquid between the two gloves, such liquid indicative of a breach of one of the gloves.

Embodiment 17: The sterilely packaged set of gloves of one of the packaged glove embodiments, wherein the outer glove is a hybrid polymer of polyisoprene and polychloroprene selected to have greater translucency than a polyisoprene glove of equal thickness.

Embodiment 18: The sterilely packaged set of gloves of one of the packaged glove embodiments, wherein the inner glove is colored the same as the outer glove. Same coloring means that visual observation against the same background sees no substantial difference.

Embodiment 19: A sterilely packaged set of right and left glove-in-gloves, the glove-in-gloves comprising: (I) an outer glove having a thumb and a plurality of fingers, further comprising crotches between adjacent fingers and thumb; and (II) an inner glove having a thumb and a plurality of fingers with finger tips, further comprising crotches between adjacent fingers and thumb, the inner glove having a size about ¼ to 1 size units larger than the outer glove, the inner glove being disposed inside the outer glove, the finger tips of the inner glove and the outer glove being substantially aligned; wherein the gloves are enfolded with a packaging material such that the material can be unfolded to present the right glove-in-glove on the right side and the left glove-in-glove on the left side, laid out on the packaging material, and wherein the glove-in-glove provides greater user comfort than a glove-in-glove of equal size.

Embodiment 20: A sterilely packaged set of right and left glove-in-gloves, the glove-in-gloves comprising: (1) an outer glove having a thumb and a plurality of fingers, further comprising crotches between adjacent fingers and thumb; and (2) an inner glove having a thumb and a plurality of fingers with finger tips, further comprising crotches between adjacent fingers and thumb, the inner glove having essentially the same size as the outer glove, the inner glove being disposed inside the outer glove, the finger tips and crotches of the inner glove and the outer glove being substantially aligned; wherein the gloves are enfolded with a packaging material such that the material can be unfolded to present the right glove-in-glove on the right side and the left glove-in-glove on the left side, laid out on the packaging material, and wherein the inner glove has a lesser cross-sectional thickness than the outer glove such that the glove-in-glove provides greater user comfort than a glove-in-glove of equal cross-sectional thickness.

Embodiment 21: A method of donning the gloves of any of the foregoing embodiments, comprising unfolding the packaging material such that the material presents the right glove-in-glove on the right side and the left glove-in-glove on the left side, laid out on the packaging material, and thereafter donning the gloves on a user.

It is to be understood that various changes and modifications to the embodiments described herein will be apparent to those skilled in the art. Such changes and modifications can be made without departing from the spirit and scope of this disclosure and without demising the attendant advantages. It is, therefore, intended that such changes and modifications be covered by the appended claims.

All references, including publications, patent applications, and patents, cited herein are hereby incorporated by reference to the same extent as if each reference were individually and specifically indicated to be incorporated by reference and were set forth in its entirety herein.

The invention claimed is:

1. A sterilely packaged set of right and left glove-in-gloves, each glove-in-glove comprising:
   an outer glove having a thumb and a plurality of fingers, further comprising crotches between adjacent fingers and thumb; and
   an inner glove having a thumb and a plurality of fingers with finger tips, further comprising crotches between adjacent fingers and thumb, wherein the inner glove, as found in a packaging material, being disposed inside the outer glove with the finger tips of the inner glove and the outer glove being aligned;
   wherein the gloves are enfolded with the packaging material such that the material can be unfolded to present the right glove-in-glove on the right side and the left glove-in-glove on the left side, laid out on the packaging material.

2. The sterilely packaged set of gloves of claim 1, comprising the inner gloves having a size about ¼ to 1 size units larger than the outer gloves, wherein the finger tips are aligned, and wherein the glove-in-glove provides greater user comfort than a glove-in-glove of equal size.

3. The sterilely packaged set of gloves of claim 1, comprising the inner gloves having a size the same as the outer gloves, wherein the finger tips and crotches are aligned.

4. The sterilely packaged set of gloves of claim 3, wherein the inner gloves has a lesser cross-sectional thickness than the outer gloves, such that the glove-in-glove provides greater user comfort than a glove-in-glove of equal cross-sectional thickness.

5. The sterilely packaged set of gloves of claim 4, further comprising the inner glove having a cross-sectional thickness at the center of the palm of about 0.15 mm to about 0.19 mm and the outer glove having a cross-sectional thickness of about 0.16 mm to about 0.21 mm.

6. The sterilely packaged set of gloves of claim 1, comprising the inner glove having a size that is one-quarter to one-half a size smaller than the outer glove, wherein the crotches and the finger tips are aligned.

7. The sterilely packaged set of gloves of claim 1, wherein the inner glove is colored the same as the outer glove.

8. The sterilely packaged set of gloves of claim 1, wherein the glove-in-gloves are packaged cuff-folded to facilitate donning.

9. The sterilely packaged set of gloves of claim 1, wherein the glove-in-gloves are packaged so that the length of the glove-in-gloves is presented after unfolding the packaging material.

10. A sterilely packaged set of right and left glove-in-gloves, the glove-in-gloves comprising:
    an outer glove having a thumb and a plurality of fingers, further comprising crotches between adjacent fingers and thumb; and
    an inner glove having a thumb and a plurality of fingers with finger tips, further comprising crotches between adjacent fingers and thumb, the inner glove having a size about ¼ to 1 size units larger than the outer glove, wherein the inner glove, as found in a packaging material, being disposed inside the outer glove with the finger tips of the inner glove and the outer glove being substantially aligned;
    wherein the gloves are enfolded with the packaging material such that the material can be unfolded to present the right glove-in-glove on the right side and the left glove-in-glove on the left side, laid out on the packaging material, and wherein the glove-in-glove provides greater user comfort than a glove-in-glove of equal size.

11. The sterilely packaged set of gloves of claim 10, wherein the glove-in-gloves are packaged cuff-folded to facilitate donning.

12. The sterilely packaged set of gloves of claim 10, wherein the glove-in-gloves are packaged so that the length of the glove-in-gloves is presented after unfolding the packaging material.

13. A method of donning the gloves of one of claim 10, comprising unfolding the packaging material such that the material presents the right glove-in-glove on the right side and the left glove-in-glove on the left side, laid out on the packaging material, and thereafter donning the gloves on a user.

14. A sterilely packaged set of right and left glove-in-gloves, the glove-in-gloves comprising:
   an outer glove having a thumb and a plurality of fingers, further comprising crotches between adjacent fingers and thumb; and
   an inner glove having a thumb and a plurality of fingers with finger tips, further comprising crotches between adjacent fingers and thumb, the inner glove having essentially the same size as the outer glove, wherein the inner glove, as found in a packaging material, being disposed inside the outer glove with the finger tips of the inner glove and the outer glove being substantially aligned;
   wherein the gloves are enfolded with the packaging material such that the material can be unfolded to present the right glove-in-glove on the right side and the left glove-in-glove on the left side, laid out on the packaging material, and wherein the inner glove has a lesser cross-sectional thickness than the outer glove such that the glove-in-glove provides greater user comfort than a glove-in-glove of equal cross-sectional thickness.

15. The sterilely packaged set of gloves of claim 14, wherein the glove-in-gloves are packaged cuff-folded to facilitate donning.

16. The sterilely packaged set of gloves of claim 14, wherein the glove-in-gloves are packaged so that the length of the glove-in-gloves is presented after unfolding the packaging material.

17. The sterilely packaged set of gloves of claim 1, comprising at least one of a natural rubber latex said inner glove and a natural rubber latex said outer glove; a natural rubber latex said inner glove and a synthetic latex said outer glove; a synthetic latex said inner glove and a natural rubber latex said outer glove; or a synthetic latex said inner glove and a said synthetic latex outer glove.

18. The sterilely packaged set of gloves of claim 1, wherein the inner glove is colored to accentuate visual recognition of liquid between the two gloves, such liquid indicative of a breach of one of the gloves.

19. The sterilely packaged set of gloves of claim 1, wherein the outer glove is a hybrid polymer of polyisoprene and polychloroprene selected to have greater translucency than a polyisoprene glove of equal thickness.

20. A method of donning the gloves of claim 1, comprising unfolding the packaging material such that the material presents the right glove-in-glove on the right side and the left glove-in-glove on the left side, laid out on the packaging material, and thereafter donning the gloves on a user.

* * * * *